(12) United States Patent
Nguyen et al.

(10) Patent No.: US 8,580,935 B2
(45) Date of Patent: Nov. 12, 2013

(54) ULTRA-FAST CHROMATOGRAPHY

(75) Inventors: Reno T. Nguyen, Rancho Cucamonga, CA (US); Scott Anderson, Lindenhurst, IL (US); Ian Chappell, Over Kellet (GB)

(73) Assignee: Alltech Associates, Inc., Columbia, MD (US)

( * ) Notice: Subject to any disclaimer, the term of this patent is extended or adjusted under 35 U.S.C. 154(b) by 747 days.

(21) Appl. No.: 12/528,670

(22) PCT Filed: Feb. 21, 2008

(86) PCT No.: PCT/US2008/002300
§ 371 (c)(1),
(2), (4) Date: Mar. 11, 2010

(87) PCT Pub. No.: WO2008/106043
PCT Pub. Date: Sep. 4, 2008

(65) Prior Publication Data
US 2010/0167374 A1 Jul. 1, 2010

Related U.S. Application Data

(60) Provisional application No. 60/903,691, filed on Feb. 26, 2007.

(51) Int. Cl.
*C07K 1/22* (2006.01)
*B01D 15/08* (2006.01)
(52) U.S. Cl.
USPC ............................ 530/417; 530/344; 210/661
(58) Field of Classification Search
USPC .................................. 530/417, 344; 210/661
See application file for complete search history.

(56) References Cited

U.S. PATENT DOCUMENTS

| | | | |
|---|---|---|---|
| 3,917,527 A | 11/1975 | Shaltiel | |
| 4,289,690 A | 9/1981 | Pestka et al. | 260/112 R |
| 4,415,631 A | 11/1983 | Schutijser | 428/405 |
| 4,477,492 A | 10/1984 | Bergna et al. | 427/215 |

(Continued)

FOREIGN PATENT DOCUMENTS

| | | | |
|---|---|---|---|
| EP | 0128 733 | 12/1984 | C12N 15/16 |
| EP | 0 162 462 | 12/1989 | C07K 3/20 |

(Continued)

OTHER PUBLICATIONS

Kuriyama et al., "Efficient peptide purification by HPLC—effect of pore size, particle size and chemistry," Peptide Science 2004, The Proceedings of the Joint Meeting of 1st Asia-Pacific International Peptide Symposium and the 41st Japanese Peptide Symposium (APIPS-JPS), pp. 211-214, 2004.*

(Continued)

*Primary Examiner* — Rosanne Kosson
(74) *Attorney, Agent, or Firm* — Beverly J. Artale (57) ABSTRACT

The present invention relates to a chromatographic method of separating biological material comprising, providing chromatographic media comprising inorganic oxide particles having an average diameter of about 2 microns or less and an average pore diameter of 300 Å or more; applying a solvent comprising said biological material to said media, wherein said biological material is reversibly bonded to said media; and eluting said biological material from said media with a solvent in less than about 2 minutes for biological material having a molecular weight of less than about 100,000 Daltons.

8 Claims, 9 Drawing Sheets

10 Repeat Injections of Synthetic Peptides

(56) References Cited

U.S. PATENT DOCUMENTS

| | | | |
|---|---|---|---|
| 4,737,292 A | 4/1988 | Ritacco et al. | 210/656 |
| 4,773,994 A | 9/1988 | Williams | |
| 4,891,133 A | 1/1990 | Colvin, Jr. | 210/198.2 |
| 4,909,941 A | 3/1990 | Poll et al. | 210/635 |
| 4,959,340 A | 9/1990 | Williams | B01J 20/22 |
| 5,019,270 A | 5/1991 | Afeyan et al. | 210/656 |
| 5,213,683 A | 5/1993 | Mann | 210/198.2 |
| 5,451,660 A | 9/1995 | Builder et al. | 530/344 |
| 5,462,659 A | 10/1995 | Saxena et al. | 210/198.2 |
| 5,585,236 A | 12/1996 | Bonn et al. | 435/5 |
| 5,667,675 A | 9/1997 | Hatch et al. | 210/198.2 |
| 5,833,861 A | 11/1998 | Afeyan et al. | 210/656 |
| 6,001,260 A | 12/1999 | Hatch et al. | 210/656 |
| 6,045,697 A | 4/2000 | Girot et al. | 210/635 |
| 6,074,556 A | 6/2000 | Van Davelaar | 210/198.2 |
| 6,090,278 A | 7/2000 | Lally et al. | 210/198.2 |
| 6,190,560 B1 | 2/2001 | Mann | 210/656 |
| 6,475,388 B1 | 11/2002 | Gjerde et al. | 210/635 |
| 6,558,539 B1 | 5/2003 | Mann | 210/198.2 |
| 6,736,974 B1 | 5/2004 | Mann | 210/656 |
| 6,872,302 B2 | 3/2005 | Aste | 210/198.2 |
| 7,008,532 B2 | 3/2006 | Shalon et al. | 210/198.2 |
| 7,132,053 B2 | 11/2006 | Hauck et al. | 210/656 |
| 7,238,282 B2 | 7/2007 | Perreault et al. | 210/198.2 |
| 2002/0098595 A1 | 7/2002 | Lubman et al. | 436/178 |
| 2003/0155300 A1 | 8/2003 | Afeyan et al. | 210/656 |
| 2004/0007530 A1 | 1/2004 | McNeff et al. | |
| 2005/0161399 A1 | 7/2005 | Dillon et al. | 210/635 |
| 2006/0070954 A1 | 4/2006 | Martosella et al. | 210/656 |
| 2006/0186049 A1 | 8/2006 | Boyes et al. | 210/656 |
| 2006/0219616 A1 | 10/2006 | Noyes et al. | 210/198.2 |

FOREIGN PATENT DOCUMENTS

| | | | |
|---|---|---|---|
| EP | 0 635 301 | 1/1995 | B01J 20/32 |
| WO | 8910177 | 11/1989 | B01D 15/08 |
| WO | 02074791 | 9/2002 | C07K 1/20 |

OTHER PUBLICATIONS

Illustrated Dictionary of Immunology, 2nd ed., J. M. Cruse and R. E. Lewis, Eds., Taylor and Francis Group, Boca Raton, 2003, pp. 320-321.*

Journal of Chromatography 458 (1988), pp. 281-286; New Packing and Column for Fast Protein High-Performance Liquid Chromatography by Szczerba and Holdoway.

IUPAC Compendium of Chemical Terminology—Peak Width (in chromatography), 1997.

* cited by examiner

Human Proteins

Closely Related Insulin Variants

Fig. 6 Peptides

Phosphopeptides and Fibrinopeptide

Fig. 8

ULTRA-FAST CHROMATOGRAPHY

CROSS REFERENCE TO RELATED APPLICATION

This application claims the benefit of U.S. Patent Application Ser. No. 60/903,691 filed Feb. 26, 2007.

BACKGROUND OF THE INVENTION

The present invention relates to the separation of biological compounds or biomolecules utilizing reverse-phase chromatographic media.

Biological compounds, such as proteins, have become important in a variety of research or analytical applications, as well as commercial applications, such as drug candidates for various therapeutic uses. One of the greatest challenges lies in the development of cost effective and efficient processes for separation of such biological materials. While many methods are now available for separation of such materials, crude products contain not only the desired product but also closely related impurities that are difficult to separate from the desired product. Moreover, biological sources of these products usually include complex mixtures of materials that include various target compounds that are present in small amounts, and may also vary in size and shape.

Generally, biological materials are produced by cell culture, using either mammalian or bacterial strains engineered to produce the materials of the interest by insertion of a recombinant plasmid containing the gene for that protein. Since the strains used are living organisms, they must be fed with a complex growth medium, containing sugars, amino acids and growth factors that are usually supplied from preparations of animal serum. Separation of the desired biomolecule from the mixture of compounds fed to the cells and from the byproducts from the cells themselves to a purity sufficient for use as a human therapeutic poses a formidable challenge. Usually, the separation procedure is multi-step requiring expensive apparatus and chromatographic media.

Procedures for purification of biomolecules from cell debris initially depend on the sight of expression of the biomolecule. Some biomolecules may be secreted directly from the cell into the surrounding growth media, while others are made intra-cellularly. For the latter biomolecules, the first step of a purification process involves lysing or destruction of the cell, which can be done by a variety of methods, including mechanical shear, osmotic shock, or enzymatic treatments. Such destruction releases the entire contents of the cell into the homogenate, and in addition produces sub-cellular fragments that are difficult to remove due to their small size. Usually, these are removed by differential centrifugation or by filtration.

After a clarified solution containing the biomolecule of interest has been obtained, its separation from the other proteins produced by the cell is usually attempted using a combination of different chromatography techniques. These techniques separate mixtures of biomolecules on the basis of their charge, degree of hydrophobicity, or size. Several different chromatography media are available for each of these techniques, allowing accurate tailoring of the purification scheme to the particular biomolecule involved. Affinity chromatography, which exploits a specific interaction between the biomolecules to be purified in a second biomolecule, such as a specific antibody, may also be a separation technique for some biomolecules.

The essence of each of the separation methods is that biomolecules can be caused either to move at different rates through chromatographic media, achieving a physical separation that increases as they pass further through the media, or to adhere selectively to the separation media, being then differentially eluted by different solvents. In some cases, the desired biomolecule is separated from impurities when the impurities specifically adhere to the media, and the biomolecule of interest does not.

The major performance measures of chromatography techniques are productivity and peak resolution. Productivity refers to specific throughput. It is a measure of the mass of solute that can be processed per unit volume of chromatography matrix. Generally, productivity improves with increases in the surface area per unit volume of the matrix, the rate of solute mass transfer to the sorbent surface, the rate of adsorption and desorption, and the fluid flow velocity through the matrix. Resolution is a measure of the degree of purification that a system can achieve. It is specified by the difference in affinity among solutes in the mixture to be separated and by the systems inherent tendency towards dispersion or band spreading. Affinity of the solutes is controlled by the nature in the process liquid and the chemical properties of the chromatography media. Band spreading is controlled primarily by the geometry of the chromatographic media (e.g. the surface area, particle size, etc.) and the mass transfer rates from the solute to the media surface during the chromatographic procedure.

The application of modern liquid chromatographic techniques by high performance liquid chromatographic (HPLC) has led to an improvement of separation, characterization, and purification of biomolecules. Liquid chromatographic using a reverse phase packing has been found to be an effective tool in both qualitative and quantitative analysis for biological substances in blood, serum, or plasma. Typically, the reverse phase packing material is made up of bonding alkyl groups to porous inorganic oxides, e.g., silica, and most typically the packing is a pore silica having octadecylsilane bonded to it. The porous silica particles are available in a variety of forms, with different sizes of particle and pore size within the particle. The size of particle chiefly determines the packing properties of the material, which determine the rate of flow and the backpressure when the material is used as a column. The pore size, however, determines the size of biological material that has access to the interior of the pore. Typically, pore sizes vary from 100 to 500 Angstroms in size. The size of the particle may depend upon the nature of the separation process. A mixture of water and organic solvent are used to elute molecules of interest. Biomolecules are often loaded under highly aqueous conditions to maximize their binding to the reversed-phase material. These molecules will elute at the threshold organic solvent concentration. One means for their elution involves a gradient separation whereby the organic solvent content is increased per unit time.

In analytical chromatography, peak resolution is of paramount importance and efforts have been made to minimize band spreading and maximize peak resolution. Efforts have also been made to increase the speed of separation of biomolecules in order to allow for expedited analysis that is needed to conduct competitive research in proteomics. Higher flow rates have been utilized to achieve higher speed of biomolecule separation, but such processes run at much higher pressures (e.g., above 5,000 psi) that cannot be implemented in standard HPLC equipment.

There have been numerous efforts of utilizing inorganic porous media to separate biological materials using high performance liquid chromatography (HPLC). See for example U.S. Pat. Nos. 4,289,690 and 4,959,340. Additionally, U.S.

Pat. No. 5,451,660 describes the use of reverse phase high-pressure liquid chromatography for the purification of polypeptides. In such a process, the different components of the mixture introduced into the column possess different respective degrees of solubility in the stationary phase (chromatographic media) and in the mobile phase (the mixture passing through the column). As the mobile phase flows over the stationary phase, there is an equilibrium in which the sample components are partitioned between the stationary phase and the mobile phase. As the mobile phase passes through the column, the equilibrium is constantly shifted in favor of the mobile phase. This occurs because the equilibrium mixture, at any time, is exposed to fresh mobile phase and partitions into the fresh mobile phase. As the mobile phase is carried down the column, the mobile phase is exposed to fresh stationary phase and partitions into the stationary phase. A separation of a mixture of components occurs because the mixture of components has slightly differently affinities for the stationary phase and/or solubilities in the mobile phase, and therefore, has different partition equilibrium values. Thus, the mixture of components passed down the column at different rates.

In U.S. Pat. No. 5,585,236, ion pair reverse-phase high-pressure liquid chromatography is described as a process for separation DNA using a non-poly separation media, wherein the process utilizes a counter-ion agent and an organic solvent to release the DNA from the separation media. More recently, analysis and separation of RNA molecules has been performed using matched ion polynucleotide chromatography. See U.S. Pat. No. 6,475,388 B1.

Profusive chromatography has been utilized to increase the efficiency in chromatographic separations by increasing the surface area of the chromatographic media and the fluid flow velocity through the media in order to increase the liquid through the column. See U.S. Pat. No. 5,833,861. This is accomplished using chromatographic media possessing a first pore set having a great mean diameter than the members of a second pore set.

Heretofore, there has been no HPLC process that provides for efficient separation of biological substances combined with the advantages of high speed of biomolecule separation. Therefore, there is a need for a separation process for such biological materials that allows for high separation speed as well as increased recovery of the target biological material that may be utilized in analytical, preparative and process chromatographic applications.

SUMMARY OF THE INVENTION

The present invention relates to a chromatographic method of separating biological material comprising, providing chromatographic media comprising inorganic oxide particles having an average diameter of about 2 microns or less and an average pore diameter of 300 Å or more; applying a solvent comprising the biological material to the media, wherein the biological material is reversibly bonded to the media; and eluting the biological material from the media with a solvent in less than about 2 minutes while generating a back pressure of less than 3000 psi.

In another embodiment, the present invention relates to a chromatographic method of separating biological material comprising providing chromatographic media comprising inorganic oxide particles having an average diameter of about 2 microns or less and an average pore diameter of 300 Å or more; applying a solvent comprising the biological material to the media, wherein the biological material is reversibly bonded to the media; and eluting the biological material from the media with a solvent in less than about 2 minutes for biological material having a molecular weight of less than about 100,000 Daltons.

In another embodiment, the present invention relates to a chromatographic method of separating biological material comprising, providing chromatographic media comprising inorganic oxide particles having an average diameter of about 2 microns or less and an average pore diameter of 300 Å or more; applying a solvent comprising the biological material to the media, wherein the biological material is reversibly bonded to the media; and eluting the biological material from the media with a solvent in less than about 2 minutes with a chromatographic peak width of the eluted biological material being less than or equal to 0.1 minutes.

In a further embodiment, the present invention relates to a chromatographic method of separating at least one antibody comprising, providing chromatographic media comprising inorganic oxide particles; applying a solvent comprising the antibody to the media, wherein the antibody is reversibly bonded to the media; and eluting the antibody from the media with a solvent in less than about 4 minutes, wherein the antibody remains intact after elution.

In an even further embodiment, the present invention provides for a chromatographic method of separating antibodies comprising: providing chromatographic media comprising inorganic oxide particles; applying a solvent comprising the biological material to the media, wherein the biological material is reversibly bonded to the media; and eluting the biological material from the media with a solvent in less than about 4 minutes with a chromatographic peak width of the eluted biological material being less than or equal to about 0.5 minutes.

DETAILED DESCRIPTION OF THE INVENTION

The present invention relates to improved processes for purifying biological compounds.

It must be noted that as used herein and in the appended claims, the singular forms "a", "and", and "the" include plural referents unless the context clearly dictates otherwise. Thus, for example, reference to "a protein" includes a plurality of such proteins and reference to "protein" includes reference to one or more proteins and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that can occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

By the term "biological compound" as used herein refers to amino acid containing compounds, such as proteins and peptides and also includes non-peptidyl compounds as used herein "peptide" refers to a molecule of up to about 30 covalently bonded amino acids including natural and unnatural amino acids of the L-isomeric form of D-isomeric, as well as derivatives and/or analogues thereof. Examples of peptides include compounds, such as enkephalin, somatostatin, somatopin and alpha-MSH. Other peptides that may be purified according to a method of the subject invention include but are not limited to, a list of peptides set forth in PCT International Publication number WO 02/074791 A1, the entire subject matter of which is incorporated herein by reference.

Proteins typically have a molecular weight of 10,000 or greater and peptides possess a molecular weight of less than 10,000 and they are also known as polypeptides. These compounds may be obtained naturally or synthetically.

As used herein, "protein" or "polypeptide" refers to peptides having more than 30 amino acids covalently bonded together. The polypeptides or proteins may be homologous to the whole cell or may be exogenous, meaning that they are heterologous, i.e., foreign to the whole cell being utilized, such as a human protein produced by a Chinese Hamster ovary cell or by a bacterial cell, or yeast polypeptide produced by different yeast or a bacterial or mammalian cell such as those set forth in U.S. Pat. No. 5,451,660, the entire subject matter of which is incorporated herein by reference. Examples of bacterial polypeptides or proteins include alkaline phosphatase and β-lactamase. Examples of mammalian polypeptides or proteins include compounds such as Renin a growth hormone, including human growth hormone bovine growth hormone; growth hormone releasing factor; parathyroid hormone; thyroid stimulating hormone; lipoproteins; alpha-1-antitrypsin; insulin A-chain, insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; hemoglobins; atrial natmietic factor; lung surfactant; a plasminogen activator, such as urokinase or human urine or tissue-type plasminogen activator (t-PA); bombesin thrombin; hemopoietic growth factor; tumor necrosis factor-alpha and -beta; enkephalinase; RANTES (regulated on activation normally T-cell expressed and secreted); human macrophage inflammatory protein (MIP-I-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inihibin; activin; vascular endothelial growth factor (VEGF); receptors for hormones or growth factors; integrin; protein A or D, rheumatoid factors; a neurotropbic factor such as bone-derived neurotrophic factor (BDNF), neurotro-phin-3, -4, -5, or -6 (NT-3, NT-4, NT-5, or NT-6), or a nerve growth factor such as NGF-P; platelet-derived growth factor (PDGF); fibroblast growth factor such as aFGF and bFGF; epidermal growth factor (EGF), transforming growth factor (TGF) such as TGF-alpha and TGF-beta, including TGF-β1, TGF-β2, TGF-β3, TGF-β4, or TGF-β65; insulin-like growth factor-I and -II (IGF-I and IGF-II); des (I-3) -IGF-I (brain IGF-I), insulin-like growth factor binding proteins; CD proteins such as CD-3, CD-4, CD-8 and CD-19; erythropoietin; osteoinductive factors; immunotoxins; a bone morphogenetic protein (BMP); an interferon such as interferonalpha, -beta, and -gamma; colony stimulating factors (CSFs), e.g., M-CSF, GM-CSF, and G-CSF; interleukins (ILs), e.g., IL-I to IL-10; superoxide dismutase; T-cell receptors; surface membrane proteins; decay accelerating factor; viral antigen such as; for example, a portion of the AIDS envelope; transport proteins; homing receptors; addressins; regulatory proteins; antibodies or immunoglobulins, such as IgG, IgM, IgA, IgD, and IgE; and fragments of any of the above-listed polypeptides.

Polypeptides of interest are those that are easily produced in cells with a minimum of proteolysis and need not be glycosylated for their intended utility. Examples of such mammalian polypeptides include IGF-I, IGF-II, brain IGF-I, growth hormone, relaxin chains, growth hormone releasing factor, insulin chains or pro-insulin, urokinase, immunotoxins, NGF, NT-5, RANTES, MIP-I-alpha, vascular endothelial growth factor, an IGF-I binding protein, a GH binding protein, and antigens. Particularly preferred mammalian polypeptides include IGF-I, brain IGF-I, growth hormone, a neurotrophin such as NGF, NT-3, NT-4, m-5, and NT-6, including NT-5, an IGF-I binding protein, vascular endothelial growth factor, or RANTES. The most preferred mammalian polypeptide is IGF-I, including full-length IGF-I and brain IGF-I. As used herein, "IGF-1" refers to insulin-like growth factor-1 from any species, including bovine, ovine, porcine, equine, and preferably human, in native sequence or in variant form (such as des-1-3-IGF-I, or brain IGF-I) and recombinantly produced. One method for IGF-I is described in EP 128,733 published Dec. 19, 1984.

Synthetic peptides may also be separated utilizing the subject invention. Such peptides include, but are not limited to, short synthetic peptides, e.g., growth hormone releasing peptides (GHRPs), etc.

As used herein, "non-peptidal compound" refers to an organic or inorganic compound that is not composed of amino acids and possesses a molecular weight of between about 100 and 30,000 Daltons. The compound is preferably an organic compound and includes antibiotics, such as vancomycins, cephalosporins, penicillins, and the like; other organic molecules that may be purified according to the invention include, but are not limited to, polyene macrolides, teypenes, alkaloids, carbohydrates, oligonucleotides, and the like. An oligonucleotide is a short length of DNA or RNA composed of relatively few nucleotide bases.

As used herein, "buffer" refers to a solution containing the buffer that resists changes in pH through acid-base congregate components. Examples of materials utilized to prepare buffers include free acids such as citric, phosphoric, maleic, malonic, phthalic, salicylic, fumaric, dimethyl malonic, mandelic, malic, formic, tartaric, itaconic, lactic, barbituric, butyric, ascorbic, succinic, benzoic, propionic, acetic, such as trifluoroacetic, etc. Suitable free bases for forming buffers include triethylamine, imidazole, brucine, tricine, glycinamide, listidine, ethanolamine, glycine, ethylamine, dimethylamine, and the like. Those of ordinary skill in the art will readily recognize that many other acids and bases may be used to prepare such buffers. Typically, buffers possess a pH between about 2.0 and about 12.0, and preferably between about 2.0 and about 10.0, and more preferably between about 2.0 and about 7.0 is typically used for reversed-phase silica resin.

As used herein, "solvent" refers to alcohols and aprotic solvents, as set forth in U.S. Pat. No. 6,475,388 B1, the entire subject matter of which is incorporated herein by reference. Alcohols include those with 1 to 10 carbon atoms, such as methanol, ethanol, iso-propanyl, n-propanol, butanol, ethylene glycol, polyethylene glycol etc. Aprotic solvents include such compounds as dimethyl sulfoxide (DMSO) dimethyl formamide (DMF), N-methylpyrrolidone (NMP), tetrahydrofuran (THF), dioxanes, nitriles, esters, ethers, etc. These are product solvents, which may be utilized alone or in conjunction with alcohols as defined herein. Preferred solvents include methanol, ethanol, iso-propanol, n-propanol, acetonitrile and mixture thereof. Typically, the buffer is prepared in water and is commonly mixed with organic solvents for reversed-phase separations.

In the process according to this invention for separating a biological compound from other components in a mixture, there are at least two steps. In the first, the mixture is loaded into a reverse-phase liquid chromatography column. The mixture may contain a number of biological components, such as carbohydrates, lipids, proteins, peptides, polypeptides, nucleic acids, and the like. The mixture may also contain closely related isomers of the target biological compound to be separated, such as regioisomers, geometric isomers, stereoisomers, and the like.

As mentioned herein, the biological compound to be separated may be carbohydrate, lipid, protein, peptide, polypeptide, or nucleic acid. Preferably, the biological compound is protein or peptide.

The chromatographic column utilized in the process of the present invention may be an analytical, preparative or process column. As used herein, "analytical" column refers to columns that are used to purify 1 ng to 10 mg, "preparative" column refers to columns that are used to purify 1 to 200 mg, and "process" column refers to columns that are used to purify 200 mg and above. Typically, the diameter of an analytical column ranges between about 2 mm and about 5 mm. Typically, the diameter of a preparative column ranges between about 10 mm and about 22 mm. The diameter of a process column typically ranges from about 50 mm to about 1000 mm. The column diameter utilized in the present invention may be between about 2 mm and 2 m, preferably between about 10 mm and about 200 mm, and more preferably, between about 20 mm and about 150 mm and even more preferably, between about 22 and about 100 mm.

The chromatographic media or stationary phase utilized in the process of the present invention is a porous inorganic oxide in the form of particles or beads. The particles may have a diameter of between about 1 micron to about 30 microns, preferably between about 1 micron to about 10 microns, and more preferably, between about 1 micron to about 5 microns, and even more preferably, between about 1 and about 2 microns. The particles may have a pore size between about 50 Angstroms to about 1000 Angstroms, preferably between about 100 Angstroms to about 1000 Angstroms, and more preferably, from about 300 Angstroms to about 1000 Angstroms. The BET surface area of the particles utilized according to the present invention may be about 50 to about 500 $m^2/g$, and preferably, about 50 to about 125 $m^2/g$. The surface areas set forth herein are measured by the nitrogen BET method. The particles may be spherical or irregular. The inorganic oxide particles are preferably porous silica prepared from silica gel.

The surface of the inorganic oxide particles may be treated in a fashion to form hydrocarbon entities bonded thereto. This renders the surface hydrophobic and allows the biological substance alkyls to be reversibly attached to the particles. The length of the hydrocarbon entities may comprise alkyls having a length of from $C_1$ to $C_{18}$ groups, or the entities may include phenyl derivatives, aminoalkyl or aminophenyl derivatives, silanes, diols, etc. Such treatment is described in U.S. Pat. Nos. 3,917,527; 6,045,697; 4,773,994; 4,477,492; 4,959,340 and 4,415,631.

A preferred media, VYDAC® ProZAP™, is available from Grace Davison, 2051 Waukegan Road, Deerfield, Ill. 60015, USA.

The separation process of the present invention may be conducted under low pressure, medium pressure or high pressure. Preferably, the process of the present invention is conducted at pressures above atmospheric pressure. One of the advantages of the present invention lies in the ability to perform the biological compound or biomolecule separation using HPLC at pressures that are not extremely high (e.g., less than 5000 psi) so that the process may be performed using most existing HPLC systems.

The column length must be scaled properly to the column diameter. In general, this is an empirical determination that may be readily made by those of ordinary skill in the art. The factors that may be important in determining the relationship between column diameter and column length include particle size, type of elution (e.g., isocratic as compared to gradient solution).

The mobile phase, which includes a mixture solvent and buffer, is mixture introduced into the column includes the target biological compound as well as other components, such as impurities, as mentioned herein, and also includes solvent and buffer in an amount of from about 0.05 to about 0.15 percent by volume, and more preferably about 0.08 to about 0.12 percent by volume of the mixture. The solvent may be an aqueous buffered solution, such as a solution of trifluoroacetic acid, heptafluorobutyric acid or phosphoric acid. Preferably, the solvent is trifluoroacetic acid. The pH of the mobile phase is preferably within the range of about pH2 to about pH9, more preferably about pH 2 to about pH 7.

The amount of biological compound loaded onto the column is generally between about 0.01 g molecule/liter bed volume to about 70.0 g molecule/liter bed volume, preferably between about 0.02 g molecule/liter bed volume to about 40.0 g molecule/liter bed volume, more preferably, between about 0.05 g molecule/liter bed volume to about 30.0 g molecule/liter bed volume.

The linear velocity of the column may vary between about 150 cm/hour to about 2000 cm/hr, and preferably, between about 300 cm/hour to about 1500 cm/hour and even more preferably between about 600 to about 1200 cm/hour during the elution process, i.e., removing the biological compound from the chromatographic media. It should be noted that the flow rate depends on the molecule phase viscosity, media head or particle size, biological compound binding efficiency to the media, operating pressure of the process, etc. The process may be conducted under pressure in a range from about 50 to about 5000 psi, preferably, from about 500 to about 4000 psi, and more preferably, from about 700 to about 3000 psi, and even more preferably, from about 1000 to about 2800 psi.

In the next step of the present invention, the biological compound is eluted from the column with a buffer and/or solvent. The eluant may be in the form of an aqueous solution containing a solvent as defined herein in an amount of about 5 to about 50% (v/v), preferably about 10 to about 40% (v/v) of the solution and may have a pH of from about 2.0 to about 12.0, preferably between about 2.0 and about 10.0, and more preferably, between about 2.0 to about 7.0. The organic solvent may be acetonitrile, ethanol, iso-propanol, or n-propanol or combinations thereof. The temperature for elution may be about room temperature or about 25° C., although higher or lower temperatures may be employed.

An advantage of the present invention lies in the ability to separate biological compounds quite rapidly while maintaining low backpressure (i.e., the pressure generated in the chromatography column as a result of the eluant flowing through the media in the chromatography column). For example, most biological compounds (e.g., biomolecules having a molecular weight less than about 100,000 Daltons) may be separated in less than about 2 minutes, preferably less than about 1.5 minutes, and more preferably less than about 1.2 minutes. For biological compounds that are larger in size (e.g., above 100,000 Daltons) such as antibodies, they may be separated according to the present invention in less than about 5 minutes, preferably less than about 4 minutes, and even more preferably less than about 3.5 minutes.

Figure 9:
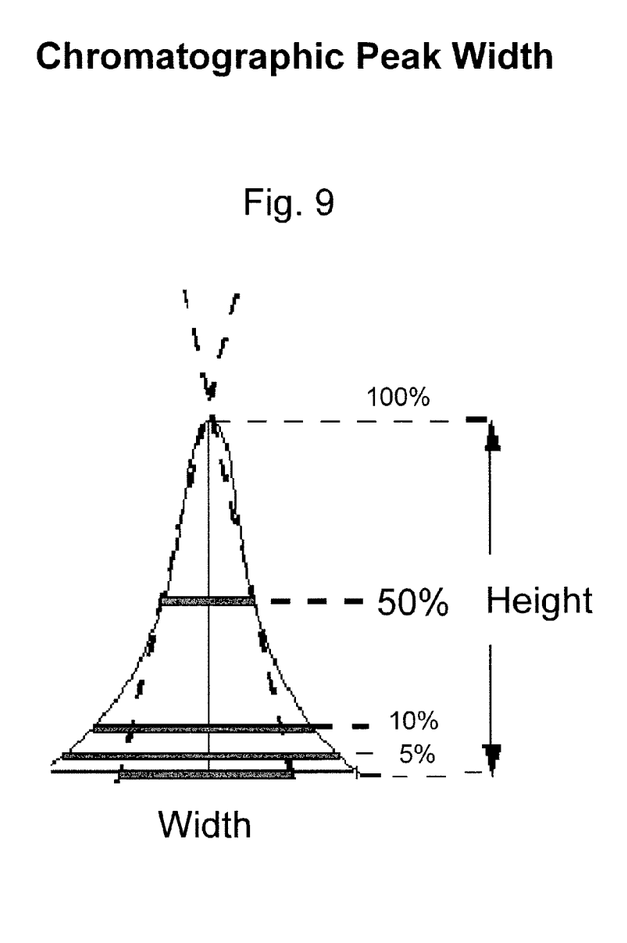
FIG. 9 illustrates peak width in a chromatogram for the separation of a biomolecule.

The high speed of biological compound separation according to the present invention provides for very narrow chromatographic peak width for each compound or biomolecule. As used herein, "peak width" is defined as the width of the chromatographic band produced during elution of the compound from the media in the column. Narrow or small peak widths usually represent efficient separation of biomolecules. Peak width is typically measured at half the height of the peak, which is the width of the peak at 50% peak height. Peak width is described in "Compendium of Chemical Terminology: lupac Recommendations" (1987) Victor Gold, Kurt L. Loening, Alan D. McNaught, Pamil Sehmi. Published by Science and Behavior Books. FIG. 9 illustrates the definition of peak width and such measurement may be determined using Dionex Chromeleon HPLC software. Peak tangents are drawn from the turning points of the ascending and the descending flanks. Then the points of intersection with the baseline are calculated. Measures of peak width include base width and peak widths at 5, 10, and 50% of the peak height. In contrast to the base width, the peak widths at 5, 10, and 50% of the peak height are not only measured up to the point of intersection with the two tangents, but up to the signal curves. Determining the peak width is only possible if the peak is resolved at least to half the height. Peak width at 50% of peak height is used in the present invention.

According to the present invention, most biological compounds (e.g., biomolecules having a molecular weight less than about 100,000 Daltons) have a peak width of less than about 0.1 minutes, preferably less than about 0.07 minutes, and more preferably less than about 0.05 minutes. For biological compounds that are larger in size (e.g., above 100,000 Daltons) such as antibodies, they may have a peak width of less than about 2.0 minutes, preferably less than about 1.0 minute, and even more preferably less than about 0.5 minute.

In a further embodiment, the present invention relates to a chromatographic method of separating at least one antibody comprising, providing chromatographic media comprising inorganic oxide particles; applying a solvent comprising the antibody to the media, wherein the antibody is reversibly bonded to the media; and eluting the antibody from the media with a solvent in less than about 5 minutes, wherein the antibody remains intact after elution. As used herein, "intact" means an antibody that is not dissociated into individual polypeptide units. For maintaining an intact antibody, no reducing agent such as 2-mercaptoethanol or dithiothreitol is utilized. Antibody solubility may be improved at a higher elution temperature of 70 to 80° C.

The eluted biological compound may be further processed depending on the desired final product. In some instances, the biological compounds may need only buffer exchange or concentration prior to their intended use. In other instances, the biological compounds may need further purification after the separation process of the current invention prior to their intended use. For example, any purification method known to one of ordinary skill in the art may be utilized for further processing. In general, techniques including, but not limited to, ammonium sulfate precipitation, centrifugation, ion exchange chromatography, affinity chromatography, gel filtration, reverse phase chromatography, recrystallization and adsorption chromatography, ultra filtration, etc. May be used to further purify the biological compounds.

EXAMPLES

The following Examples are given as specific illustrations of the claimed invention. It should be understood, however, that the invention is not limited to the specific details set forth in the Examples. All parts and percentages in the Examples, as well as in the remainder of the specification, are by weight unless otherwise specified.

Example I

In this Example, high performance chromatographic silica comprised of spherical porous (i.e., pores having diameters of 500 Å) particles of 1.5 µm is tested in a chromatographic column to determine its ability to separate various biological substances, such as proteins. The silica includes a surface treatment that yields a layer $C_{18}$ silane covalently bonded to the silica surface, which renders the particles hydrophobic. This silica is available from Grace Davison as VYDAC® ProZAP™.

Figure 1:
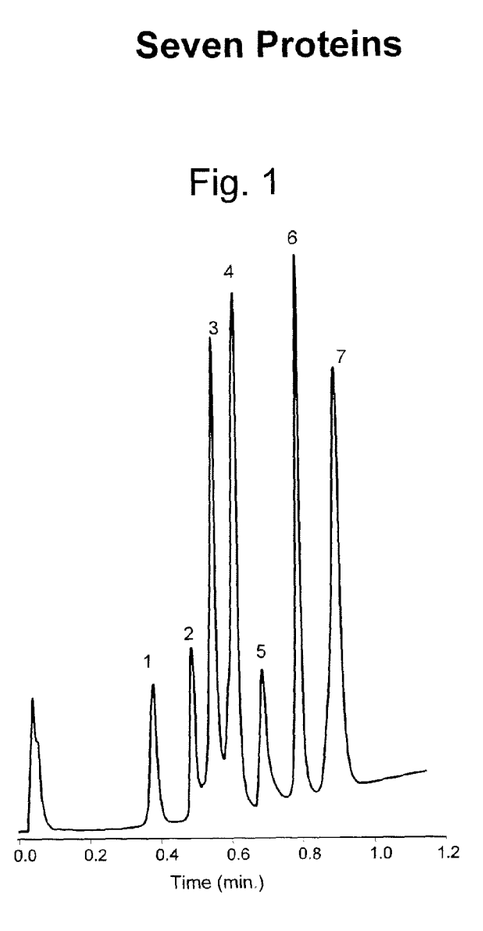
FIG. 1 illustrates a chromatogram for the separation of various proteins in the process of the present invention.

Reversed-phase chromatography is utilized as the separation technique with the VYDAC® ProZAP™ media. Various proteins, listed in TABLE 1, are injected into a VYDAC® ProZAP™ column (2.1 mm×10 mm) under the following conditions: a mobile phase including solvent A comprising 0.1% v/v TFA in water; and solvent B comprising 0.085% v/v TFA in acetonitrile. A gradient process is used wherein the column is equilibrated at 23% solvent B for 2 minutes; followed by increasing from 23% up to 75% solvent B in 1.0 minute; holding the flow of solvent B at 75% for 0.1 minute; and then reducing the flow of solvent B from 75 to 23% in 0.1 minute. The flow rate is 0.8 ml/minute. The column is run at a room temperature of 25° C. The detection is performed using a UVD 170S detector (available from Dionex Corp., Sunnyvale, Calif.) at 280 nm. A Dionex HPLC system (P580 HPG high-pressure gradient, binary pump available from Dionex Corp.), Rheodyne Manual Injector (available from IDEX Corp.), and CHROMELEON® data system (available from Dionex Corp.), are also utilized in the analyses. In order to achieve fast gradients and minimize re-equilibration times, the binary pump is necessary for precise, high-pressure mixing gradient formation and low delay volume. Extra column volume are minimized as follows: (1) the tubing from the injector to the column and from the column to the detector should be as short as practical and have an internal ID of 0.12 mm (0.005"); (2) the standard flow cell>10 µL is replaced with a cell<5-µL. All injection volumes do not exceed a maximum of 5 µL for 2.1 mm ID columns. Column backpressure is 185 bar (2680 psi) as measured using the Dionex HPLC system. The results are shown in FIG. 1 and TABLE 1.

TABLE 1

| Peak # | Protein | Molecular Weight (Da) | Amount Injected (ng) | Retention Time (min.) | Peak Width (min.) |
|---|---|---|---|---|---|
| 1 | Ribonuclease | 13,700 | 37 | 0.40 | 0.021 |
| 2 | Bovine insulin | 5,700 | 37 | 0.51 | 0.017 |
| 3 | Bovine cytochrome c | 12,200 | 37 | 0.57 | 0.015 |
| 4 | Lysozyme | 14,300 | 4 | 0.64 | 0.019 |
| 5 | Bovine serum albumin | 66,400 | 37 | 0.72 | 0.021 |
| 6 | Bovine carbonic Anhydrase II | 29,000 | 37 | 0.83 | 0.013 |
| 7 | Ovalbumin | 45,500 | 37 | 0.94 | 0.025 |

Example II

Figure 2:
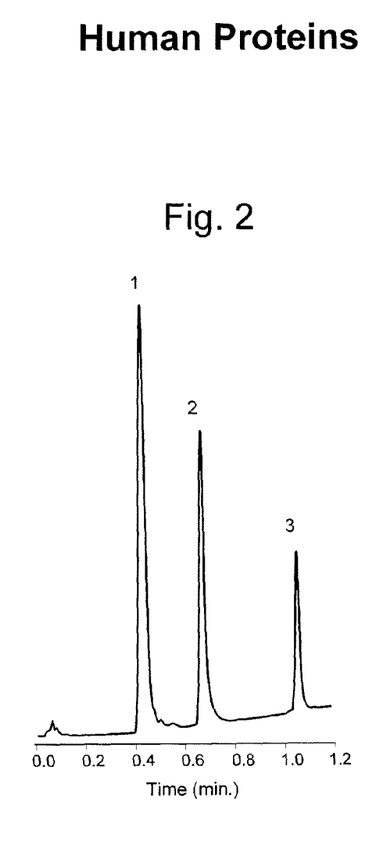
FIG. 2 illustrates a chromatogram for the separation of human proteins in the process of the present invention.

The testing method and column as set forth in EXAMPLE I is used except that the gradient process is modified as follows: the column is equilibrated at 25% solvent B for 2 minutes; followed by increasing from 25% up to 75% solvent B in 1.0 minute; holding the flow of solvent B at 75% for 0.1 minute; and then reducing the flow of solvent B from 75 to 25% in 0.1 minute. Column backpressure is 185 bar (2680 psi). The results, as shown in FIG. 2 and TABLE 2, clearly demonstrate that fast protein separations are achieved as in EXAMPLE I.

TABLE 2

| Peak # | Protein | Molecular Weight (Da) | Amount Injected (ng) | Retention Time (min.) | Peak Width (min.) |
|---|---|---|---|---|---|
| 1 | Human insulin | 5,800 | 1700 | 0.43 | 0.030 |
| 2 | Human serum albumin | 66,500 | 1700 | 0.67 | 0.020 |
| 3 | Human growth hormone | 22,100 | 300 | 1.06 | 0.018 |

Example III

Figure 3:
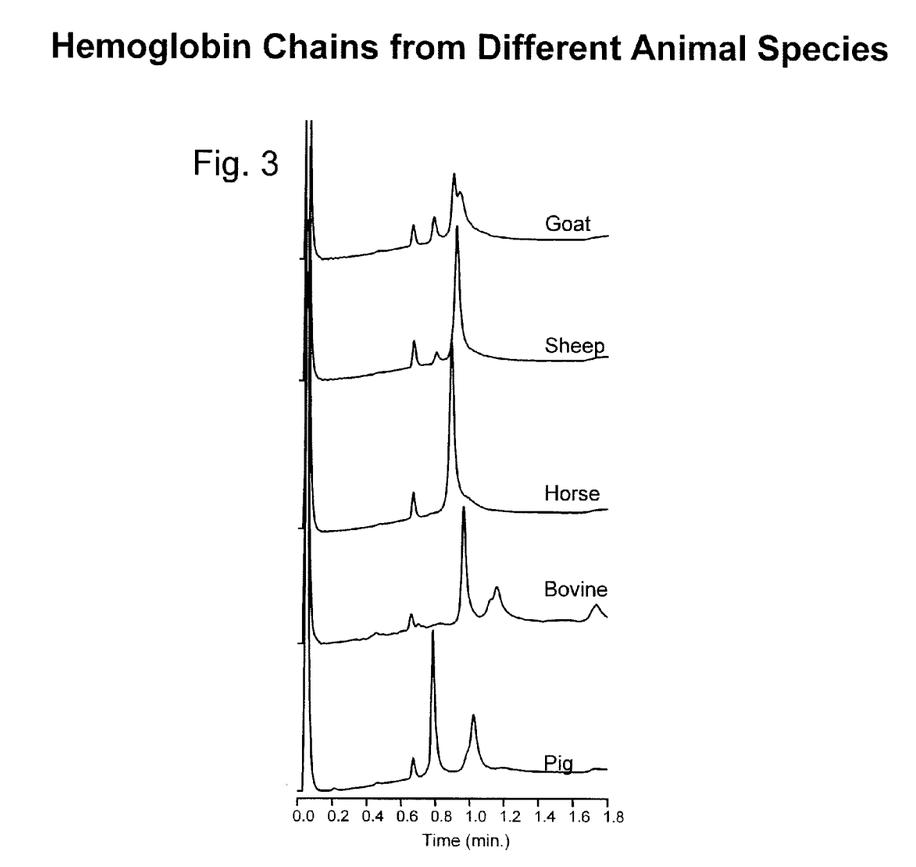
FIG. 3 illustrates a chromatogram for the separation of various hemoglobin chains from different animal species in the process of the present invention.

The testing method and column as set forth in EXAMPLE I is used except that the detection is at 220 nm and the gradient process is modified as follows: the column is equilibrated at 25% solvent B for 2 minutes; followed by increasing from 25% up to 45% solvent B in 0.5 minute; holding the flow of solvent B at 45% for 1.0 minute; followed by increasing from 45% up to 75% solvent B in 0.1 minute; holding the flow of solvent B at 75% for 0.1 minute; and then reducing the flow of solvent B from 75 to 25% in 0.1 minute. Column backpressure is 185 bar (2680 psi). The results, as shown in FIG. 3 and TABLE 3, clearly demonstrate that fast protein separations are achieved as in EXAMPLES I and II. Moreover, hemoglobins from different animal species may be quickly analyzed and compared.

TABLE 3

| Pig Hemoglobin Component | Molecular Weight (Da) | Retention Time (min.) | Peak Width (min.) |
|---|---|---|---|
| Heme | 615 | 0.65 | 0.019 |
| Alpha-chain | 15,000 | 0.77 | 0.024 |
| Beta-chain | 16,000 | 0.99 | 0.040 |

Example IV

Figure 4:
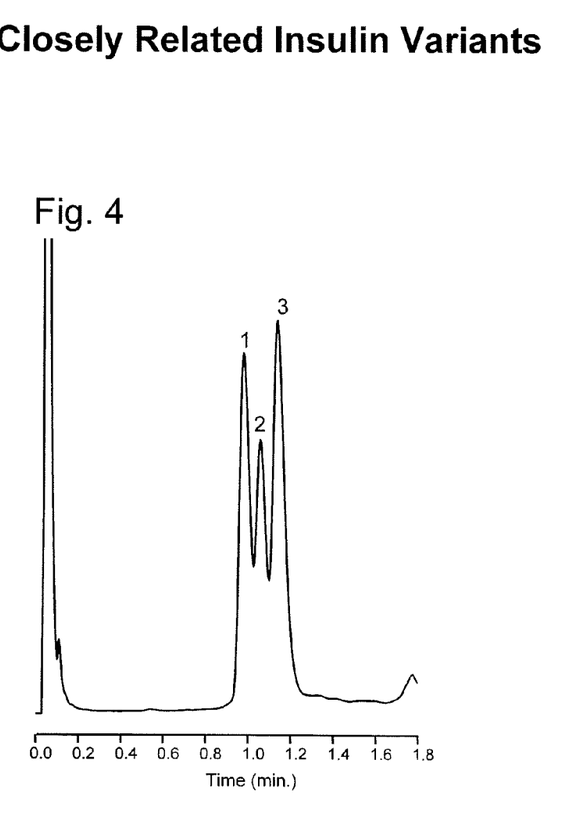
FIG. 4 illustrates a chromatogram for the separation of closely related insulin variants in the process of the present invention.

The testing method and column as set forth in EXAMPLE I is used except that the detection is at 215 nm and the gradient process is modified as follows: the column is equilibrated at 25% solvent B for 2 minutes; followed by increasing from 25% up to 30% solvent B in 1.5 minute; followed by increasing from 30% up to 50% solvent B in 0.1 minute; holding the flow of solvent B at 50% for 0.1 minute; and then reducing the flow of solvent B from 50 to 25% in 0.1 minute. Column backpressure is 170 bar (2465 psi). The results, as shown in FIG. 4 and TABLE 4, clearly demonstrate that fast protein separations are achieved as in EXAMPLES I, II, and III. Moreover, closely related insulin variants (from different animal species) may be quickly analyzed.

TABLE 4

| Peak # | Protein | Molecular Weight (Da) | Amount Injected (ng) | Retention Time (min.) | Peak Width (min.) |
|---|---|---|---|---|---|
| 1 | Bovine insulin | 5,700 | 300 | 0.98 | 0.057 |
| 2 | Sheep insulin | 5,700 | 300 | 1.06 | N/A |
| 3 | Human insulin | 5,800 | 300 | 1.14 | 0.062 |

Example V

Figure 5:
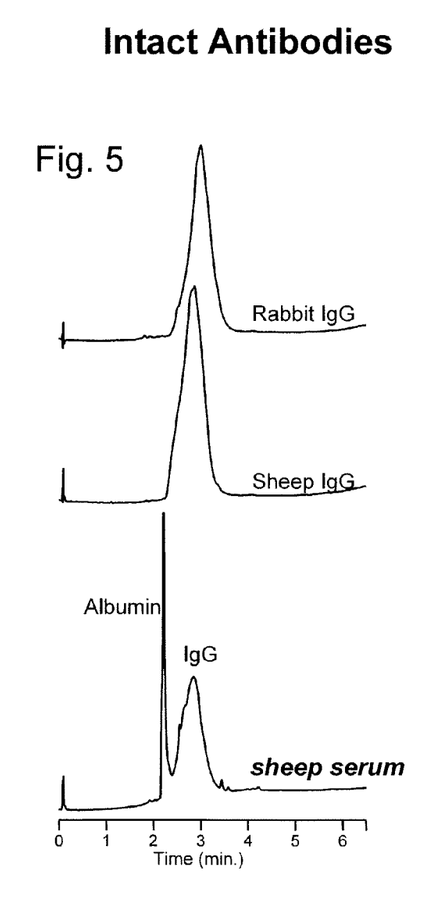
FIG. 5 illustrates a chromatogram for the separation of intact antibodies in the process of the present invention.

Intact antibodies or immunoglobulins (IgG) are injected into a VYDAC® ProZAP™ column (2.1 mm×10 mm) under the following conditions: a mobile phase including solvent A comprising 0.1% v/v TFA in water; and solvent B comprising 0.085% v/v TFA in 90:10 n-propanol:water. A gradient process is used wherein the column is equilibrated at 5% solvent B for 2 minutes; followed by increasing from 5% up to 75% solvent B in 6.0 minutes; holding the flow of solvent B at 75% for 0.5 minute; and then reducing the flow of solvent B from 75 to 5% in 0.5 minute. The flow rate is 0.5 ml/minute. The detection is performed using a UVD 170S detector (available from Dionex Corp., Sunnyvale, Calif.) at 280 nm. A Dionex HPLC system (P580 HPG high-pressure gradient, binary pump available from Dionex Corp.), Rheodyne Manual Injector (available from IDEX Corp.), Cera Column Heater (available from PJ Cobert and Associates), and CHROMELEON® data system (available from Dionex Corp.), are also utilized in the analyses. The column heater is set to a temperature of 75° C. The extra column volume is minimized as in EXAMPLE I. Column backpressure is 170 bar (2465 psi). The results, as shown in FIG. 5 and TABLE 5, demonstrate that intact, high molecular weight antibodies are rapidly chromatographed.

TABLE 5

| Antibody | Molecular Weight (Da) | Amount Injected (μg) | Retention Time (min.) | Peak Width (min.) |
|---|---|---|---|---|
| Rabbit IgG | 150,000 | 25 | 3.01 | 0.442 |
| Sheep IgG | 150,000 | 25 | 2.87 | 0.505 |

Example VI

Figure 6:
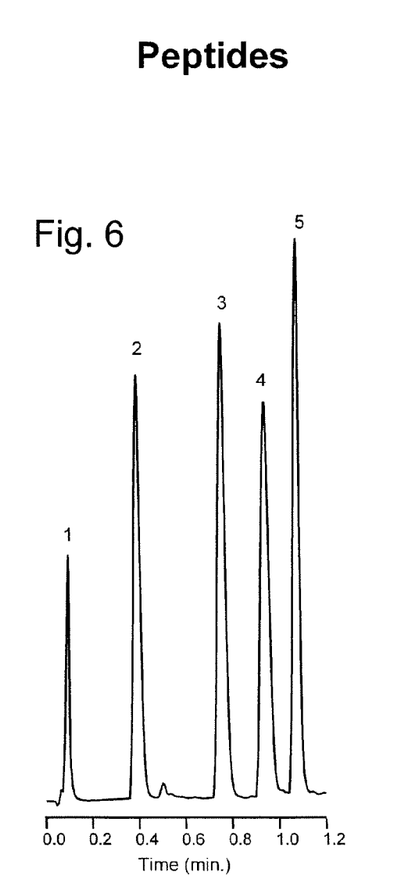
FIG. 6 illustrates a chromatogram for the separation of various peptides in the process of the present invention.

Peptides are injected into a VYDAC® ProZAP™ column (2.1 mm×10 mm) under the following conditions: a mobile phase including solvent A comprising 0.1% v/v TFA in water; and solvent B comprising 0.085% v/v TFA in 80:20 acetonitrile:water. A gradient process is used wherein the column is equilibrated at 4% solvent B for 2 minutes; followed by increasing from 4% up to 15% solvent B in 0.1 minutes; increasing from 15% up to 20% solvent B in 0.6 minute; increasing from 20% up to 50% solvent B in 0.4 minute; and then reducing the flow of solvent B from 50 to 4% in 0.1 minute. The flow rate is 0.8 ml/minute. The detection is performed using a UVD 170S detector (available from Dionex Corp., Sunnyvale, Calif.) at 215 nm. A Dionex HPLC system (P580 HPG high-pressure gradient, binary pump available from Dionex Corp.), Rheodyne Manual Injector (available from IDEX Corp.), and CHROMELEON® data system (available from Dionex Corp.), are also utilized in the analyses. The column is run at a room temperature of 25° C. The extra column volume is minimized as in EXAMPLE I. Column backpressure is 180 bar (2610 psi). The results, as shown in FIG. 6 and TABLE 6, clearly demonstrate that fast separations of peptides are achieved.

TABLE 6

| Peak # | Peptide | Molecular Weight (Da) | Amount Injected (ng) | Retention Time (min.) | Peak Width (min.) |
|---|---|---|---|---|---|
| 1 | GY | 238 | 200 | 0.09 | 0.012 |
| 2 | VYV | 379 | 600 | 0.39 | 0.028 |
| 3 | Met Enkephalin (YGGFM) | 573 | 600 | 0.76 | 0.030 |
| 4 | Leu Enkephalin (YGGFL) | 555 | 600 | 0.94 | 0.037 |
| 5 | Angiotensin II (DRVYIHPF) | 1045 | 600 | 1.08 | 0.024 |

Example VII

Figure 7:
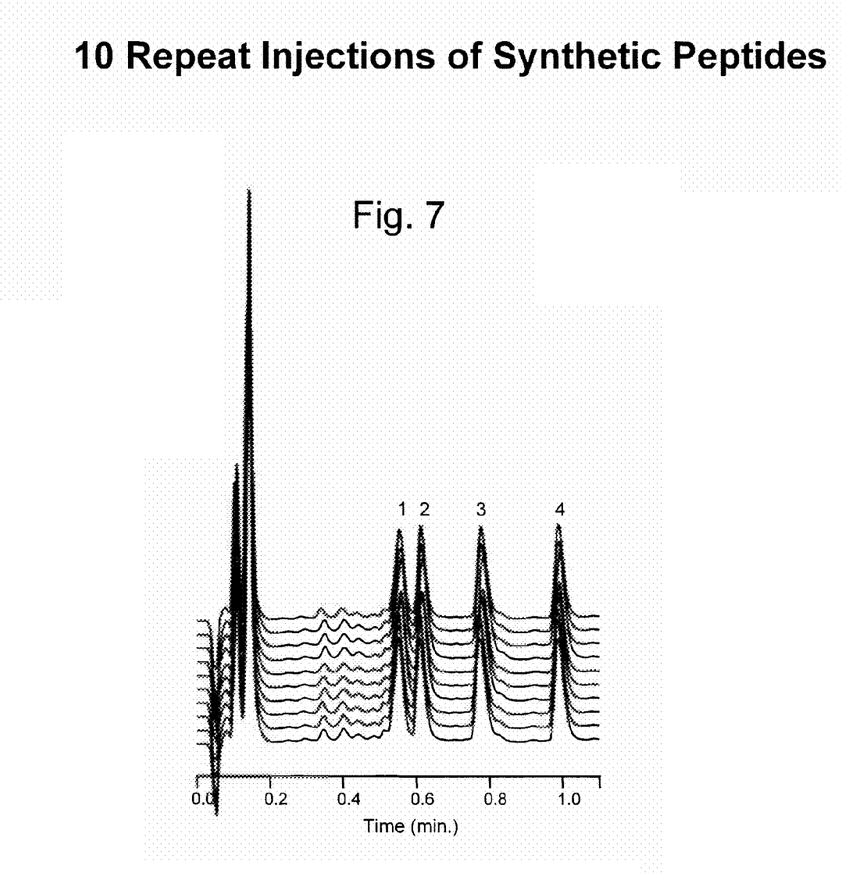
FIG. 7 illustrates a chromatogram for separations of repeated injections of various synthetic peptides in the process of the present invention.

The testing method and column as set forth in EXAMPLE VI is used. Column backpressure is 180 bar (2610 psi). The results, as shown in FIG. 7 and TABLE 7, clearly demonstrate that fast peptide separations are achieved as in EXAMPLE VI. Moreover, synthetic peptides of similar amino acid sequences are resolved.

TABLE 7

| Peak # | Peptide | Molecular Weight (Da) | Amount Injected (ng) | Retention Time (min.) | Peak Width (min.) |
|---|---|---|---|---|---|
| 1 | RGAGGLGLGK-amide | 883 | 500 | 0.56 | 0.026 |
| 2 | Ac-RGAGGLGLGK-amide | 926 | 500 | 0.61 | 0.023 |
| 3 | Ac-RGVGGLGLGK-amide | 954 | 500 | 0.78 | 0.028 |
| 4 | Ac-RGVVGLGLGK-amide | 996 | 500 | 0.99 | 0.025 |

Example VIII

Figure 8:
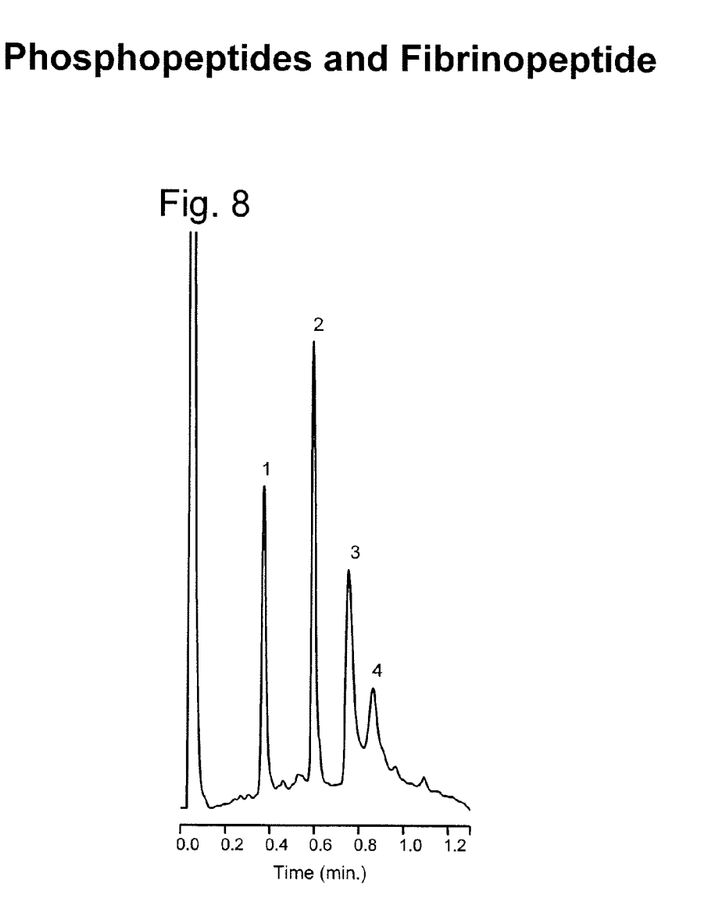
FIG. 8 illustrates a chromatogram for the separation of phosphopeptides and fibrinopeptide in the process of the present invention.

The testing method and column as set forth in EXAMPLE VI is used, except that the gradient process is modified as follows: the column is equilibrated at 12% solvent B for 2 minutes; followed by increasing from 12% up to 60% solvent B in 1.0 minute; followed by increasing from 60% up to 80% solvent B in 0.1 minute; holding the flow of solvent B at 80% for 0.2 minute; and then reducing the flow of solvent B from 80 to 12% in 0.1 minute. Column backpressure is 180 bar (2610 psi) The results, as shown in FIG. 8 and TABLE 8, clearly demonstrate that fast peptide separations are achieved as in EXAMPLES VI and VII. Moreover, phosphopeptides of various amino acid sequences and different levels of phosphorylation are resolved.

TABLE 8

| Peak # | Peptide | Molecular Weight (Da) | Amount Injected (ng) | Retention Time (min.) | Peak Width (min.) |
|---|---|---|---|---|---|
| 1 | Monophosphopeptide (FQpSEEQQTEDELQDK) | 2061 | 20 | 0.38 | 0.018 |
| 2 | [Glu$^1$]-Fibrinopeptide B (EGVNDNEEGFFSAR) | 1571 | 20 | 0.59 | 0.016 |
| 3 | Tetraphosphopeptide (RELEELNVPGEIVEpSLpSpSpSEESITR) | 3121 | 60 | 0.76 | 0.037 |
| 4 | Contaminant Peptide(s) | | | | |

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. A chromatographic method of separating biological material comprising:
   (a). providing a chromatographic medium comprising inorganic oxide particles having an average diameter of 2 microns or less and an average pore diameter of 300 Å or more;
   (b) applying a first solvent comprising said biological material to said medium, wherein said biological material is reversibly bonded to said medium; and
   (c) eluting said biological material from said medium with a second solvent in 2 minutes or less, wherein each component in the biological material has a molecular weight of 100,000 Daltons or less.

2. The method according to claim 1, wherein said biological material comprises one or more proteins and peptides.

3. The method according to claim 1, wherein said biological material comprises one or more proteins.

4. The method according to claim 1, wherein said inorganic oxide particles have an average particle size ranging from about 1.0 μm to about 2.0 μm.

5. The method according to claim 1, wherein said solvent comprises water, acetonitrile, and trifluoroacetic acid.

6. The method according to claim 1, wherein said solvent comprises 0.08 to 0.1% v/v trifluoroacetic acid in water and acetonitrile.

7. The method according to claim 1, wherein said eluting of said biological material from said medium occurs in 1.5 minutes or less.

8. The method according to claim 1, wherein said eluting of said biological material from said medium occurs in 1.2 minutes or less.

* * * * *